(12) United States Patent
Jiang et al.

(10) Patent No.: US 10,398,864 B2
(45) Date of Patent: Sep. 3, 2019

(54) METHOD AND APPARATUS FOR PROVIDING ARTIFICIAL VENTILATION TO A TRACHEA OF A PATIENT

(71) Applicant: THE GENERAL HOSPITAL CORPORATION, Boston, MA (US)

(72) Inventors: Yandong Jiang, Weston, MA (US); Robert M. Kacmarek, Boston, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 432 days.

(21) Appl. No.: 15/102,928

(22) PCT Filed: Dec. 11, 2014

(86) PCT No.: PCT/US2014/069715
§ 371 (c)(1),
(2) Date: Jun. 9, 2016

(87) PCT Pub. No.: WO2015/089270
PCT Pub. Date: Jun. 18, 2015

(65) Prior Publication Data
US 2016/0303339 A1  Oct. 20, 2016

Related U.S. Application Data

(60) Provisional application No. 61/914,734, filed on Dec. 11, 2013.

(51) Int. Cl.
*A61M 16/04* (2006.01)
*A61M 25/00* (2006.01)
(Continued)

(52) U.S. Cl.
CPC .... *A61M 16/0452* (2014.02); *A61M 16/0009* (2014.02); *A61M 16/04* (2013.01);
(Continued)

(58) Field of Classification Search
CPC ............. A61M 16/044; A61M 16/045; A61M 16/0452; A61M 25/1018;
(Continued)

(56) References Cited

U.S. PATENT DOCUMENTS 3,565,079 A * 2/1971 Jackson ................ A61M 16/04
128/207.15
3,707,151 A * 12/1972 Jackson ................ A61M 16/04
128/207.15
(Continued)

FOREIGN PATENT DOCUMENTS

GB          1153863        5/1969
WO     2010108242 A1      9/2010

OTHER PUBLICATIONS

PCT International Search Report for PCT/US2014/069715, dated Mar. 31, 2015, pp. 1-3.

*Primary Examiner* — Valerie L Woodward
(74) *Attorney, Agent, or Firm* — Tarolli, Sundheim, Covell & Tummino LLP

(57) ABSTRACT

An airway catheter ("AC") includes a catheter tube having proximal and distal tube end faces in fluid communication with a tube lumen. The distal tube end face and a portion of the tube wall collectively form a distal tube end region. A plurality of side holes extend laterally through the tube wall. An inflatable cuff is secured to the outer tube wall surface with an inner cuff volume in fluid communication with the tube lumen via the side holes. A resistor plug has proximal and distal plug end faces in fluid communication with a plug lumen and is defined laterally by a plug wall. The resistor plug is maintained within at least a portion of the tube lumen in the distal tube end region with an outer plug wall surface being at least partially in compressive contact with the inner tube wall surface.

10 Claims, 7 Drawing Sheets

US 10,398,864 B2
Page 2

(51) Int. Cl.
*A61M 25/04* (2006.01)
*A61M 25/10* (2013.01)
*A61M 16/08* (2006.01)
*A61M 16/00* (2006.01)

(52) U.S. Cl.
CPC ...... *A61M 16/0866* (2014.02); *A61M 25/007* (2013.01); *A61M 25/0068* (2013.01); *A61M 25/04* (2013.01); *A61M 2025/0073* (2013.01); *A61M 2025/1063* (2013.01); *A61M 2025/1093* (2013.01); *A61M 2209/02* (2013.01)

(58) Field of Classification Search
CPC ........ A61M 25/10181; A61M 25/0068; A61M 25/007; A61M 25/04; A61M 2015/0073; A61M 2015/1093
See application file for complete search history.

(56) References Cited

U.S. PATENT DOCUMENTS

| | | | | |
|---|---|---|---|---|
| 4,324,235 A | * | 4/1982 | Beran | A61M 16/04 128/207.15 |
| 5,318,021 A | | 6/1994 | Alessi | |
| 5,638,813 A | * | 6/1997 | Augustine | A61M 16/04 128/207.15 |
| 2008/0078399 A1 | | 4/2008 | O'Neil et al. | |

* cited by examiner

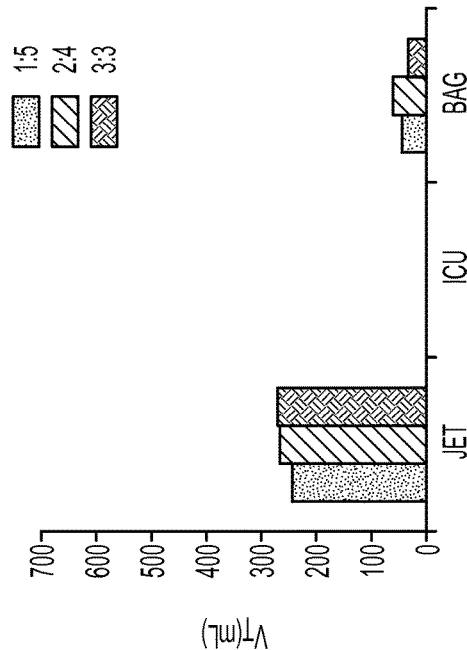
FIG. 6A
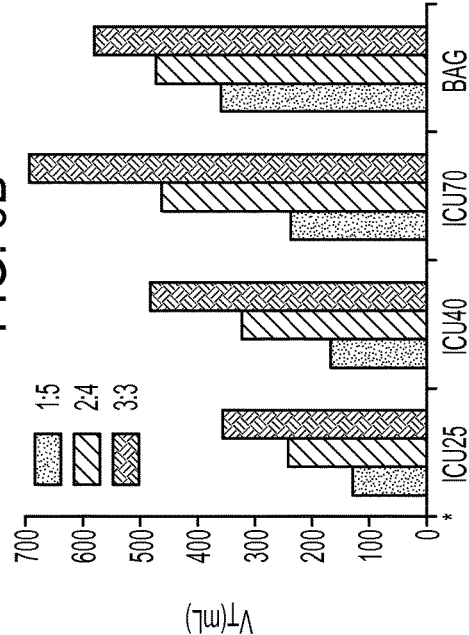
FIG. 6B
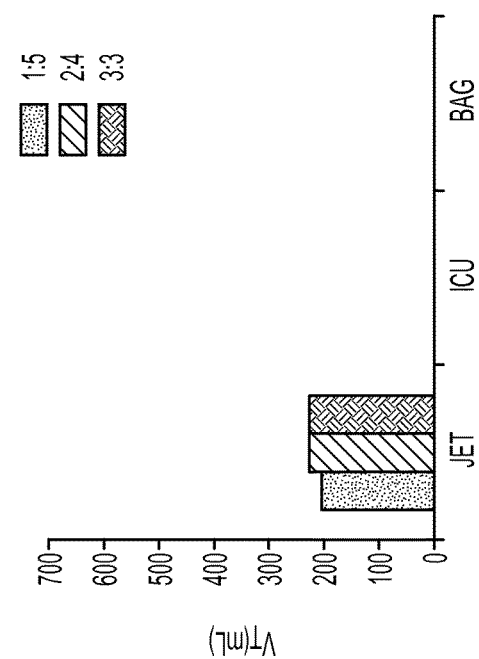
FIG. 6C
FIG. 6D

METHOD AND APPARATUS FOR PROVIDING ARTIFICIAL VENTILATION TO A TRACHEA OF A PATIENT

RELATED APPLICATION

This application claims priority from U.S. Provisional Application No. 61/914,734, filed 11 Dec. 2013, the subject matter of which is incorporated herein by reference in its entirety.

TECHNICAL FIELD

The present invention relates to an apparatus and method for assisting a patient in breathing and, more particularly, to an apparatus and method for providing artificial ventilation through a trachea of a patient.

BACKGROUND OF THE INVENTION

Airway catheters ("ACs") are widely used to facilitate extubation and re-intubation. These long, thin hollow tubes may be inserted through an endotracheal tube ("ETT") before extubation to provide continuous airway access and serve as a guide, should re-intubation be necessary following a failed extubation. Oxygen can be provided by either insufflation or jet ventilation through the distal end of the catheter and its side ports. Thus, ACs can be used to ventilate the patient as well as afford the physician additional time to consider alternative airway management strategies. This practice has reduced the incidence of extubation complications, especially in at-risk patients with head and neck pathology or undergoing maxillofacial or neck surgery.

Despite these benefits, complications can arise when using ACs. Barotrauma resulting in pneumothorax has been a major concern when using jet ventilation with ACs. One study found 11% of patients suffered barotrauma from jet ventilation with ACs. Fifteen other case studies have reported pneumothorax, cardiac arrest and death when jet ventilation via ACs were applied. The cause of these complications is often the excessive driving pressure with jet ventilation (15 to 50 psi) and/or airway obstructions. Therefore, it has been suggested that minimizing intratracheal pressure and prolonging expiratory times can reduce the risk of pneumothorax. Furthermore, jet ventilation may not be readily available in an emergency case, especially in rural health care settings or intensive care units ("ICUs"). These limitations have led to doubts on the utility of jet ventilation through an AC.

SUMMARY OF THE INVENTION

In an embodiment of the present invention, a method of providing artificial ventilation to a trachea of a patient is described. The trachea has a longitudinally oriented trachea lumen defined by a trachea wall. An airway catheter ("AC") includes an elongate, flexible catheter tube having longitudinally spaced proximal and distal tube end faces in fluid communication with a tube lumen extending longitudinally through the tube and is defined laterally by a tube wall extending between the proximal and distal tube end faces. The tube wall has laterally spaced inner and outer tube wall surfaces. The distal tube end face and a minority portion of the tube wall directly longitudinally adjacent to the distal tube end face collectively form a distal tube end region. A plurality of side holes extend laterally through the tube wall between the inner and outer tube wall surfaces. All of the side holes are located in the distal tube end region. An inflatable cuff is secured to the outer tube wall surface at two longitudinally spaced circumferences of the outer tube wall surface in the distal tube end region such that an inner volume of the cuff is in fluid communication with the tube lumen via all of the plurality of side holes. The inflatable cuff is configured for selective adjustment between inflated and deflated conditions. A reduced-diameter resistor plug has laterally spaced proximal and distal plug end faces in fluid communication with a plug lumen extending longitudinally through the resistor plug and is defined laterally by a plug wall extending between the proximal and distal plug end faces. The plug lumen has a substantially smaller inner diameter than an inner diameter of the tube lumen in the distal tube end region. The plug wall has laterally spaced inner and outer plug wall surfaces. The resistor plug is maintained within at least a portion of the tube lumen in the distal tube end region with an outer plug wall surface being at least partially in compressive contact with the inner tube wall surface. A ventilation fluid source having a selectively adjustable ventilation fluid flow pressure and direction is provided. The ventilation fluid source is operatively placed in fluid communication with the proximal tube end. At least a distal portion of the AC is arranged within the trachea lumen. Ventilation fluid from the ventilation fluid source is directed to flow in a first, distally oriented direction through the tube lumen. The diameter of the plug lumen being smaller than the diameter of the tube lumen causes a first elevated ventilation fluid pressure in a portion of the tube lumen longitudinally coincident with at least a portion of the distal tube end region by resisting passage of the ventilation fluid through the plug lumen. With the first elevated ventilation fluid pressure, at least a portion of the ventilation fluid is urged through at least one side hole and into the inflatable cuff to urge the inflatable cuff toward the inflated condition.

In an embodiment of the present invention, an airway catheter ("AC") is provided. An elongate, flexible catheter tube has longitudinally spaced proximal and distal tube end faces in fluid communication with a tube lumen extending longitudinally through the tube and is defined laterally by a tube wall extending between the proximal and distal tube end faces. The tube wall has laterally spaced inner and outer tube wall surfaces. The distal tube end face and a minority portion of the tube wall directly longitudinally adjacent to the distal tube end face collectively form a distal tube end region. A plurality of side holes extend laterally through the tube wall between the inner and outer tube wall surfaces. All of the side holes are located in the distal tube end region. An inflatable cuff is secured to the outer tube wall surface at two longitudinally spaced circumferences of the outer tube wall surface in the distal tube end region such that an inner volume of the cuff is in fluid communication with the tube lumen via all of the plurality of side holes. The inflatable cuff is configured for selective adjustment between inflated and deflated conditions. A reduced-diameter resistor plug has laterally spaced proximal and distal plug end faces in fluid communication with a plug lumen extending longitudinally through the resistor plug and is defined laterally by a plug wall extending between the proximal and distal plug end faces. The plug lumen has a substantially smaller inner diameter than an inner diameter of the tube lumen in the distal tube end region. The plug wall has laterally spaced inner and outer plug wall surfaces. The resistor plug is maintained within at least a portion of the tube lumen in the distal tube end region with an outer plug wall surface being at least partially in compressive contact with the inner tube wall surface.

BRIEF DESCRIPTION OF THE DRAWINGS

For a better understanding of the invention, reference may be made to the accompanying drawings, in which:

FIGS. 6A-6D are charts of test results using the test setup of FIG. 3; and

DESCRIPTION OF EMBODIMENTS

The invention comprises, consists of, or consists essentially of the following features, in any combination.

Figure 1A:
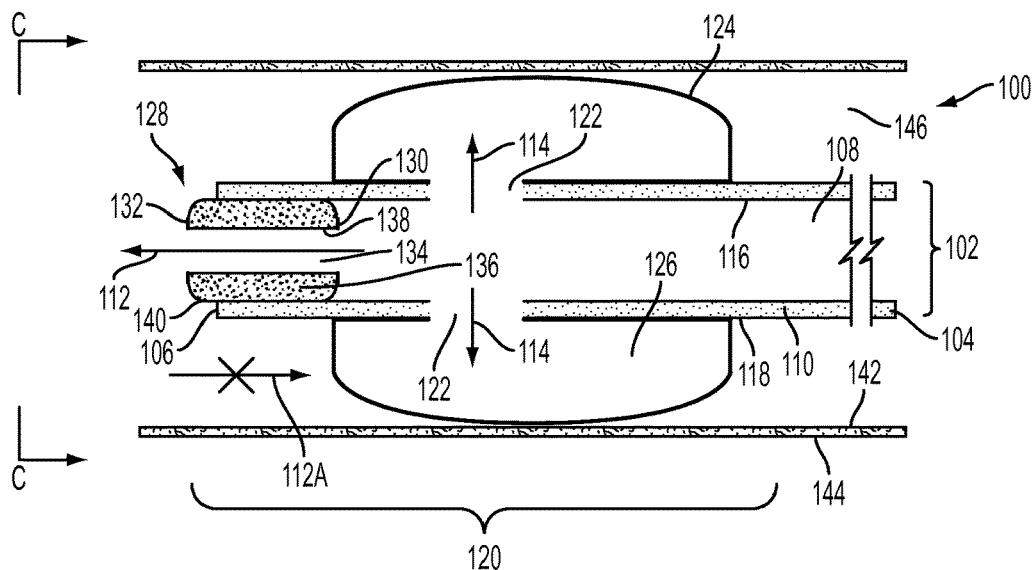
FIG. 1A is a schematic side view of one embodiment of the present invention in an example use environment and in a first, inflated condition.

In accordance with the present invention, FIG. 1A depicts an airway catheter ("AC") 100. The AC 100 includes an elongate, flexible catheter tube 102 having longitudinally spaced proximal and distal tube end faces 104 and 106, respectively, in fluid communication with a tube lumen 108. The catheter tube 102 may be obtained, for example, as the Cook Airway catheter from Cook Critical Care of Bloomington, Ind., USA. The tube lumen 108 extends longitudinally through the tube 102 and is defined laterally by a tube wall 110 extending between the proximal and distal tube end faces 104 and 106. The term "AC" is used herein for convenience to generally indicate an example device structure that can be used with the present invention. However, there is no requirement that the structure referenced herein as "AC" actually be an "airway catheter" per se. Any structure capable of being used and/or configured analogously to the structures of the present invention described herein should be considered an "AC" within the meaning of this description, even if that other structure has a different name and/or differs in other aspects of structure but can be used substantially similarly to the AC described herein.

The term "longitudinally" is used herein to indicate a horizontal direction in the orientation of, and substantially in the plane of, FIG. 1A, as shown by the longitudinal arrow 112. The term "laterally" is used herein to indicate a direction substantially perpendicular to the longitudinal arrow 112, such as the directions shown within the plane of FIG. 1A using lateral arrows 114 in addition to the "lateral" directions extending into and out of the plane of FIG. 1A.

The tube lumen 108 may be substantially of constant diameter and cross-section along an entire longitudinal length thereof. (It is contemplated, however, that even in the case of such a substantially constant tube lumen 108, a portion of the tube 102 near the proximal tube end face 104 may vary to permit operative connections to be made to the tube without destroying the otherwise substantially constant nature of the tube lumen.) It is also contemplated that the tube lumen 108 may be located non-concentrically or off-center with respect to the outer tube wall surface 118.

Optionally, the proximal tube end face 104, or any other structure of the tube 102 including or adjacent thereto, may be configured for operative connection to a ventilation fluid source (not shown), in any desired manner, to place the tube lumen 108 in fluid communication with the ventilation fluid source.

The tube wall 110 has laterally spaced inner and outer tube wall surfaces 116 and 118, respectively. The distal tube end face 106 and a minority portion of the tube wall 110 directly longitudinally adjacent to the distal tube end face collectively form a distal tube end region 120. The term "minority portion" is used herein to indicate that the distal tube end region 120 occupies (and/or is defined by) a length of the tube wall 110 which is significantly less than half the length of the entire tube 102. For example, if a tube 102 is twenty inches long, the distal tube end region 120 might be defined by the distalmost two inches of that tube. One of ordinary skill in the art would be able to provide an appropriately sized distal tube end region 120 for a particular application of the present invention.

At least one, and for many use environments of the present invention, a plurality of side holes 122 may extend laterally through the tube wall 110 between the inner and outer tube wall surfaces 116 and 118. For some embodiments of the present invention, all of the side holes 122 will be located in the distal tube end region 120. The side holes 122 may each be any suitable size, shape, or other configuration, and may be located at any desired location along the tube wall 110. One of ordinary skill in the art will be able to configure and place side holes 122 as desired for a particular application of the present invention.

An inflatable cuff 124 may be secured to the outer tube wall surface 118 at two longitudinally spaced circumferences of the outer tube wall surface in the distal tube end region 120, as is generally known in the field of catheters with inflatable cuffs. An inner volume 126 of the cuff 124 may be in fluid communication with the tube lumen 108 via some or all of the plurality of side holes 122, the inflatable cuff 124 being configured for selective adjustment between inflated and deflated conditions. The inflatable cuff 124 may be of any suitable type. For example, and as shown in the Figures, a flexible and relatively thin skin or membrane (i.e., a thin soft pliable sheet or layer) may be wrapped laterally around at least a portion of the tube 102 in a cylindrical configuration, and then the open ends of the "cylinder" thus formed are cinched around, and secured to, the outer tube wall surface 118.

The inflated condition is shown in FIG. 1A. The term "inflated" may be used to indicate a condition in which the inflatable cuff 124 is inflated to a desired degree to function as described herein, but may still be capable of accepting additional inflation fluid—"inflation" comprises partial or full status and is not intended to require full inflation in every situation.

A reduced-diameter (i.e., reduced from that of the tube lumen 108) resistor plug 128 may be provided and may have laterally spaced proximal and distal plug end faces 130 and 132, respectively. A suitable resistor plug 128 may take the form of any structure contributing to generating the below-described pressure gradient and contributing to operation of the AC 100 substantially in the manner described herein. As with any structure of the present invention, the resistor plug 128 can have any suitable shape, size, configuration, or other properties and may be made of any desired material. The proximal and distal plug end faces 130 and 132 may be in fluid communication with a plug lumen 134 extending longitudinally through the resistor plug 128. The plug lumen 134 may be defined laterally by a plug wall 136 extending between the proximal and distal plug end faces 130 and 132. When present, the plug lumen 134 has a substantially smaller inner diameter than a corresponding inner diameter of the tube lumen 108 in the distal tube end region 120. The plug wall 136 has laterally spaced inner and outer plug wall surfaces 138 and 140, respectively. The resistor plug 128, when present, is maintained within at least a portion of the tube lumen 108 in the distal tube end region 120 with an outer plug wall surface 140 being at least partially in compressive contact with the inner tube wall surface 116. For example, frictional forces developed between the outer plug wall surface 140 and the inner tube wall surface 116 can be used to partially or wholly maintain the resistor plug 128 in the position shown in the Figures, optionally with the assistance of an adhesive, set screw, interference fit structure, splaying structure, or any other desired attachment means.

The plug lumen 134 may be substantially of constant diameter and cross-section along an entire longitudinal length thereof, or the inner plug wall surface 138 may exhibit some degree of taper (toward either longitudinal direction) causing a frustoconical aspect to the plug lumen. It is also contemplated that the plug lumen 134 may be located non-concentrically or off-center with respect to the outer plug wall surface 140.

Figure 1B:
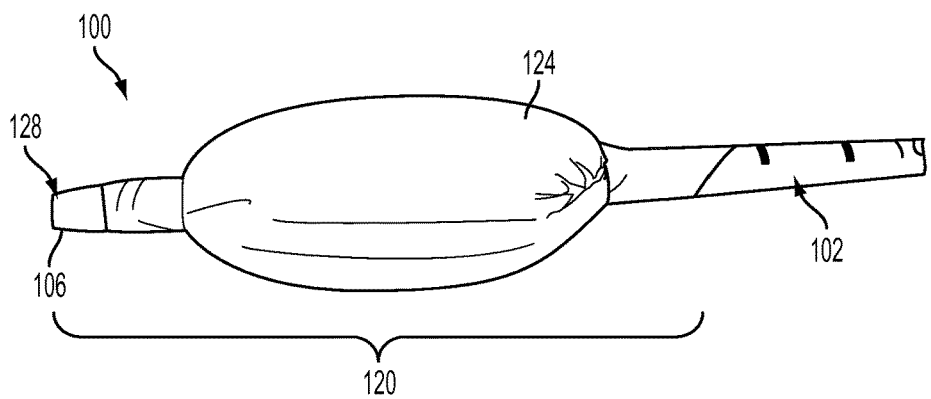
FIG. 1B is a side view of the embodiment of FIG. 1A without the example use environment.

The resistor plug 128 may be maintained within at least a portion of the tube lumen 108 in the distal tube end region 120 with an outer plug wall surface 140 being at least partially in compressive contact with the inner tube wall surface 116 and with the distal plug end face 132 being located distally from the distal tube end face 106. In other words, and as shown in FIGS. 1A-1B, the resistor plug 128 may protrude slightly distally from the tube 102.

In operation, the AC 100 is configured such that the inflatable cuff 124 cycles between the inflated and deflated conditions in coordination with, and due to the influence of, the applied air or other fluid pressure provided by the previously mentioned ventilation source. In this manner, the inflatable cuff 124 can be alternated into and out of contact with an inner wall 142 of a trachea 144 when the AC 100 is at least partially located within a longitudinally extending trachea lumen 146. This cyclical contact between the inflatable cuff 124 may help avoid pressure- and friction-caused trauma to the trachea inner wall 142 during ventilation using the AC 100. The below description of use presumes that the tube lumen 108 is in appropriate fluid contact with a source of ventilation fluid. The ventilation fluid source (not shown in FIGS. 1A-2C) may be manually or automatically controlled and powered to provide any suitable fluid such as, but not limited to, breathing gases or liquid to the AC 100.

Figure 1C:
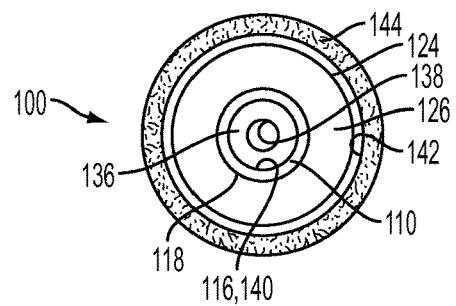
FIG. 1C is a schematic front view taken along line C-C of FIG. 1A.
Figure 2A:
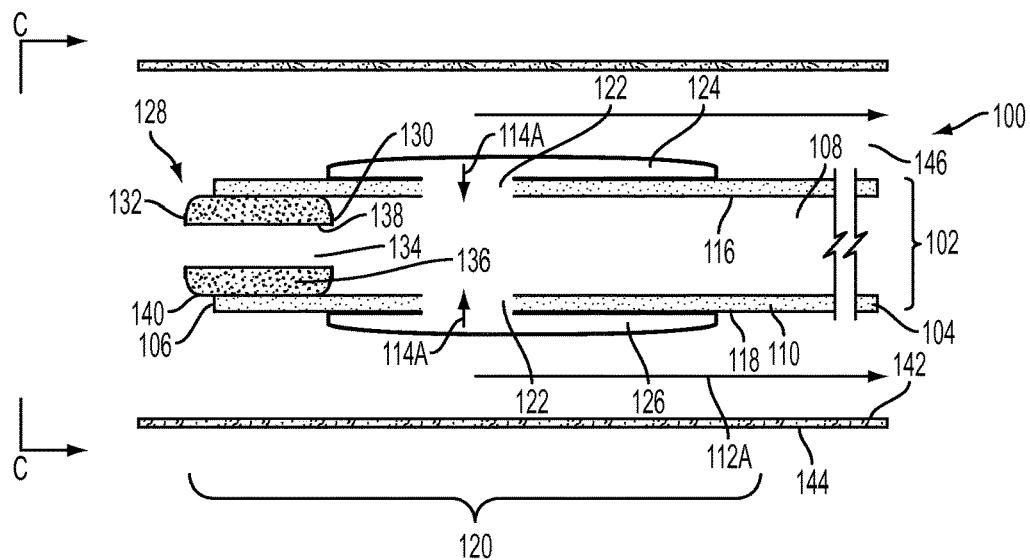
FIG. 2A is a schematic side view of the embodiment of FIG. 1A in an example use environment and in a second, deflated condition.
Figure 2B:
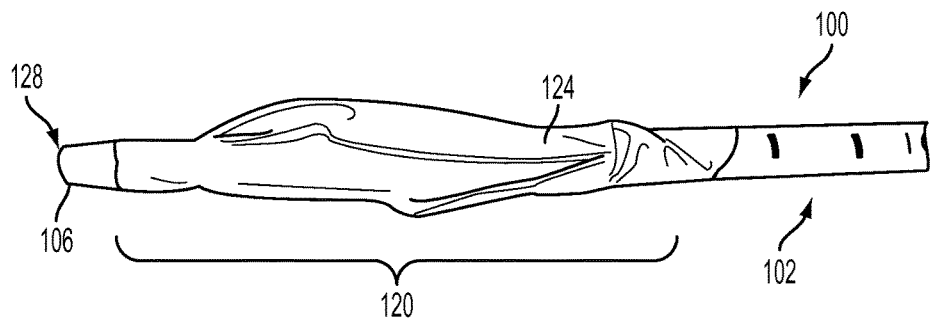
FIG. 2B is a side view of the embodiment of FIG. 2A without the example use environment.
Figure 2C:
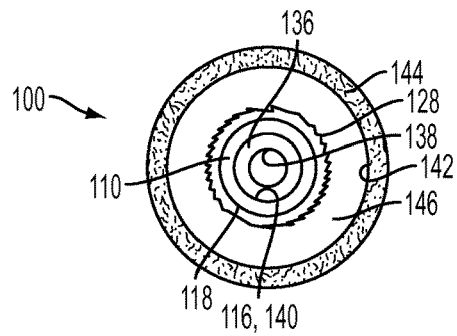
FIG. 2C is a schematic front view taken along line C-C of FIG. 2A.

In practice, the AC 100 will normally be placed within the trachea 144, in any suitable manner, in the deflated or collapsed condition shown in FIGS. 2A-2C, and with no ventilation fluid provided from the ventilation fluid source. Once the AC 100 has been advanced to a desired longitudinal position within the trachea lumen 146, the flow of ventilation fluid commences. The ventilation fluid flows in a first, distally oriented longitudinal direction (i.e., to the left in the orientation of FIGS. 1A and 2A) through the tube lumen 108 during an inspiration phase of the ventilation process. As the ventilation fluid fills the tube lumen 108 and approaches the resistor plug 128, the reduced diameter of the plug lumen 134 (as compared to the remaining, larger diameter of the tube lumen 108) resists passage of the ventilation fluid therethrough and thus causes a first elevated ventilation fluid pressure in a portion of the tube lumen 108 which is longitudinally coincident with at least a portion of the distal tube end region 120. The first elevated ventilation fluid pressure caused by the "necking down" of the available flow cross-section within the AC 100 at/near the proximal plug end face 130 forces at least a portion of the ventilation fluid through at least one side hole 122 and into the inflatable cuff 124 to urge the inflatable cuff toward the inflated condition shown in FIGS. 1A-1C. (It is noted, however, that a portion of the ventilation fluid supplied to the tube lumen 108 may flow through the plug lumen 134 and out of the AC 100 from the distal tube and plug end faces 106 and 133 during inflation of the inflatable cuff 124.)

The inflatable cuff 124 is configured to accept a predetermined volume of ventilation fluid from the plurality of side holes 122. For example, the amount of ventilation (inflation) fluid that the inflatable cuff 124 can accept could be at least partially dictated by the size of the trachea lumen 146; the size, stiffness, configuration, or any other property of the membrane forming the inflatable cuff; the size, shape, configuration of one or more side holes 122, or any other factor. At least a portion of an outer circumference of the inflatable cuff 124 can be brought into lateral contact with at least a portion of the inner wall 142 of the trachea 144 as the inflatable cuff 124 is being urged into the inflated condition.

When the inflatable cuff 124 has achieved a sufficiently inflated condition (which, as previously mentioned, need not be a maximum inflation) through presence of the ventilation fluid within the inflatable cuff, fluid pressure within the inflatable cuff rises sufficiently to resist lateral flow through the side holes 122 of ventilation fluid in excess of the predetermined (inflation) volume of ventilation fluid. The flow resistance thus provided by "feedback" from the inflatable cuff 124 causes a second elevated ventilation fluid pressure, higher than the first elevated ventilation fluid pressure, in a portion of the tube lumen 108 which is longitudinally coincident with at least a portion of the distal tube end region 120. The second elevated ventilation fluid pressure is sufficient to overcome the resistance of the reduced-diameter plug lumen 134, and that second elevated ventilation fluid pressure then urges ventilation fluid distally through the plug lumen 134 and out of the AC 100 from the distal tube and plug end faces 106 and 133. Depending upon the relative configurations of the inflatable cuff 124, side holes 122, tube 102, resistor plug 128, and/or any other components of the AC 100, the portion of ventilation fluid maintaining the inflatable cuff in the inflated condition may flow into and out of the inflated cuff during maintenance of the inflated cuff in the inflated condition. Alternately, the portion of ventilation fluid maintaining the inflatable cuff in the inflated condition may be relatively quiescent within the inflated cuff.

Once the inflatable cuff 124 has moved from the deflated condition of FIGS. 2A-2C into the inflated condition of FIGS. 1A-1C, the ventilation fluid supplied to the tube lumen 108 is urged distally through the plug lumen 134 and out of the AC 100 from the distal tube and plug end faces 106 and 132. This "ejected" ventilation fluid is operative to raise an ambient fluid pressure in an ambient space substantially distally located with respect to the AC 100, such as within portions of the patient's trachea 144 located distally from the inflated cuff 124 and/or within the patient's lungs (not shown).

In most use environments of the present invention, while the inflatable cuff 124 is held in the inflated condition, the inflatable cuff 124 substantially blocks passage of fluid (e.g., ventilation fluid, patient secretions, or any other fluids) proximally between the outer tube wall surface 116 and the inner wall 142 of the trachea 144—i.e., in a longitudinal direction toward the right, in the orientation of FIGS. 1A and 2A. In other words, substantially an entirety of the outer circumference of the inflatable cuff 124 may be placed into lateral contact with at least a portion of the inner wall 142 of the trachea 144 to substantially block fluid flow longitudinally past the inflatable cuff through the trachea. This blockage is represented by the crossed-out longitudinal arrow 112A in FIG. 1A. Fluids which do accumulate between the outer tube wall surface 116 and the inner wall 142 of the trachea 144 and distally from the inflatable cuff 124 may be suctioned out (e.g., through a suction channel of the AC 100, not shown) and/or may be permitted to remain in that space during direction and ejection of ventilation fluid distally through the plug lumen 134 and out of the AC 100 from the distal tube and plug end faces 106 and 132.

Once the inspiration phase of the ventilation process or cycle has been completed as desired (e.g., determined according to a predetermined timing pattern, some measured/sensed patient characteristics/traits, or any other factor), the ventilation fluid source switches to an expiration phase, wherein the supply of ventilation from the ventilation fluid source is slowed, terminated, or even reversed (to suction/vacuum) as compared to the inspiration phase, in order to help the patient exhale.

During the expiration phase, the tube lumen 108 is in fluid communication with the ventilation fluid source. The fluid pressure within the tube lumen 108 is selectively adjusted to have a lower pressure than the ambient fluid pressure in the ambient (i.e., surrounding or adjacent; e.g., the trachea lumen distal to the AC 100) volume or space within the trachea and distally located with respect to the AC 100. The lower pressure within the tube lumen 108 causes the ventilation fluid maintaining the inflatable cuff 124 in the inflated condition to be drawn laterally through the side holes 122 from the inflatable cuff and, optionally, longitudinally through the tube lumen 108 toward the proximal tube end face 104. Such "draining" of the ventilation fluid therefrom will urge the inflatable cuff 124 from the inflated condition toward the deflated condition.

Once the inflatable cuff 124 has been at least partially deflated, an outer circumference of the inflatable cuff will move or collapse at least partially out of contact with the inner wall 142 of the trachea 144, as shown by the laterally inwardly extending arrows 114A in FIG. 2A.

At the same time as the inflatable cuff 124 is moving from the inflated condition of FIGS. 1A-1C to the deflated condition of FIGS. 2A-2C, the at least partial deflation of the inflatable cuff and the ambient fluid pressure within the trachea lumen 146 (such as, for example, the ambient fluid pressure in an ambient space substantially distally located with respect to the AC 100) may cooperatively urge ventilation fluid from the ambient space or other portions of the trachea 144 or related structures to flow in a second, proximally oriented longitudinal direction past the outer tube wall, as shown by longitudinal arrow 112A in FIG. 2A. Optionally, the AC 100 could be configured such that the ambient fluid pressure yielded during inspiration also or instead urges ventilation fluid from the ambient space to flow in a second, proximally oriented direction through the tube lumen 108. By using the ambient space between the inner wall 142 of the trachea 144 and the outer tube wall surface 118 for fluid flow, the expiration phase of ventilation can be carried out with minimal resistance to proximally oriented ventilation flow. This co-axial flow may help facilitate a reduction of anatomic dead space (by 50% or more in some use environments) due to inspiration through the tube lumen 108 and expiration occurring through the ambient space between the inner wall 142 of the trachea 144 and the outer tube wall surface 118. Additionally, fluid secretions (such as mucous, microorganisms, or any other materials) located in or adjacent to the AC 100 within the trachea 144 can be removed during expiration by being carried in the ventilation fluid flowing in the second, proximally oriented direction and/or by a suction lumen or other feature of the AC (not shown). This may help facilitate clearance of trachea secretions or other unwanted materials within the trachea.

The below description and corresponding Figures recount and analyze an experimental procedure carried out using an AC 100 according to an aspect of the present invention.

The study was conducted on an adult tracheal/lung model with adjustable lung mechanisms. ACs 100 of sizes 14 French ("Fr") and 19 Fr were evaluated with and without the inflatable cuff 124. The inflatable cuff 124 was attached to the AC 100 at or near the distal tube end region 120 of the AC. A resistor plug 128 was placed at the distal tube end face 105 and partially occluded the tube lumen 108. The inflatable cuff 124 was in fluid communication with the tube lumen 108. The distal tube end face 106 was placed 3 cm above the carina of a tracheal model. The proximal tube end face 104 was connected to either a jet ventilator ("Jet") operated at 5, 10, 15, and 20 psi, an ICU ventilator ("ICU vent") set to pressure control with peak pressures of 25, 40, or 70 cmH$_2$O, or a manual ventilation bag ("Bag") with peak pressures of 100 to 120 cmH$_2$O. Effective V$_T$ was considered to be >100 ml.

With conventional ventilation equipment, Jet produced a mean V$_T$ of 262 ml (range: 40 ml to 631 ml) with 19 Fr, and 220 ml (24 ml to 634 ml) with 14 Fr, but the ICU vent and Bag were unable to generate effective V$_T$. With an AC 100 according to an aspect of the present invention, the ICU ventilator and Bag were both able to generate V$_T$ of 373 ml at 19 Fr (range: 224 ml to 487 ml) and 232 ml at 14 Fr (130 ml to 370 ml).

Figure 3:
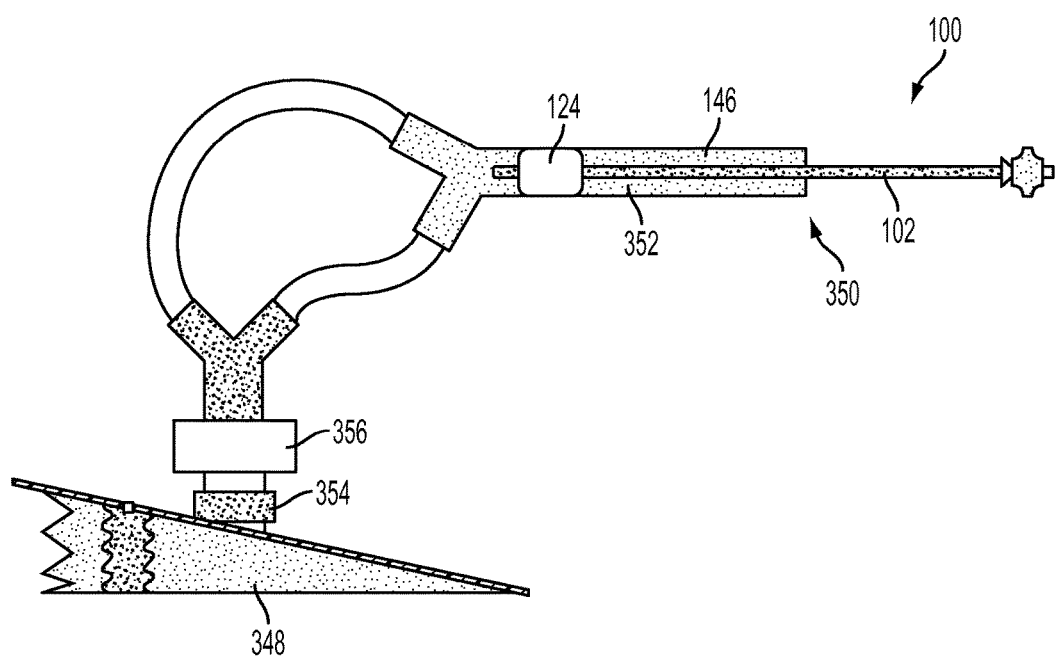
FIG. 3 is a schematic side view of a test setup for the embodiment of FIG. 1A.

The experimental setup consisted of a tracheal and lung model, as shown in FIG. 3. The lung model 348 (e.g., a dual adult TTL training/test lung, Model 1600, available from Michigan Instruments Inc., MI, USA) was connected to a distal end 350 of a tracheal model 352 (e.g., an airway demonstration model, available from Laerdal of Stavanger, Norway) with anatomical dead space of 75 mL. A Pneuflo™ (i.e., a precision airflow resistor 356 for medical apparatus available from Michigan Instruments Inc., MI, USA) was placed between the tracheal and lung models 352 and 348. The lung model 348 was adjusted to simulate three different lung mechanics: Normal (compliance 50 mL/cmH$_2$O, resistance 5 cmH$_2$O/L/s); Obstructive (compliance 60 mL/cmH$_2$O, resistance 20 cmH$_2$O/L/s); and Restrictive (compliance 20 mL/cmH$_2$O, resistance 5 cmH$_2$O/L/s).

Two types of airway catheters were tested in this study: cuffed and conventional. A Cook Airway catheter (3.0 mm-14 Fr or 3.6 mm-19 Fr, available from Cook Critical Care, Bloomington, Ind., USA) was used as a conventional catheter. A cuffed AC 100, such as that described with reference to FIGS. 1A-2C, was created from the conventional catheter by mounting a 5 cm long latex inflatable cuff 124 over the side holes 122 and inserting a 1 cm long internal resistor (such as a segment or portion of a 14 G IV catheter or 2.3 mm I.D.-11 Fr Cook Airway catheter) into the distal tip of each AC 100 (14 Fr and 19 Fr), as shown in FIGS. 1A-2C. The interior of the inflatable cuff 124 freely communicated with the tube lumen 108 of the AC 100. The cuff 124 inflated during inspiration due to pressure generated by the resistor 354 during inspiratory flow through the AC 100. The outer diameter of the inflated cuff 124 was 20, 21, and 22 mm, respectively, at driving pressures of 25, 40, and 70 cmH$_2$O in both 19 Fr and 14 Fr ACs 100. The inflated cuff 124 at least partially occluded the trachea lumen 146 of the model trachea 352. During exhalation, the inflatable cuff 124 at least partially deflated, allowing expiratory flow around the AC 100 as previously described.

The proximal end 104 of the AC 100 was connected to one of three ventilation devices: Jet, ICU vent or Bag. Jet (such as model number #00-325, available from Anesthesia Associates Inc., of San Marcos, Calif., USA) was operated at 5, 10, 15, and 20 psi, in various phases of study, using hospital central air supply. The ICU vent (such as Puritan Bennett™ 840, available from COVIDEN, of Boulder, Col., USA) was set to the pressure-controlled mode with peak inspiratory pressures of 25, 40, and 70 cmH$_2$O at various phases of study. The Bag (such as a PORTEX® 1st Response™ Adult Manual Resuscitator, available from Smiths Medical International Ltd. of the UK) provided driving pressures ranging from 100 to 120 cmH$_2$O. Ventilation was performed at a respiratory rate of 10 breaths per minute. Inspiratory to expiratory (I:E) ratios of 1:5, 2:4 and 3:3 (for 1, 2, and 3 sec inspiratory times respectively) were achieved by ventilator automatic settings or manually by the operator guided by a timer.

A flow/pressure sensor 356 (such as NICO Cardiopulmonary Management System, Model 7300, available from Respironics Corp., of Murrysville, Pa., USA) was placed between the distal end 350 of the tracheal model 352 and the model lung 348, as shown in FIG. 3. The sensor 356 was automatically calibrated prior to data collection. Pressure and air flow were continuously measured by the sensor 356 at a sampling rate of 100 Hz. $V_T$ were calculated and recorded by the monitor.

The distal tube end face 104 of the AC 100 or conventional catheter, as was being used at the time, was placed 3 cm above the carina of the trachea model. Each ventilation setting was evaluated separately using both the AC 100 and the conventional catheter. Data was continuously collected using the NICO Analysis Plus data management system corresponding to the sensor 356. For each setting, data was collected for one minute, and the last five consecutive breaths were analyzed. Data are presented as mean±standard deviation. Effective $V_T$ was considered a $V_T$ greater than 100 ml. For main effects, the general linear model for univariate analysis was used to identify the significance of the time ratio of inspiratory and expiratory and different lung mechanics on $V_T$. The Friedman test followed by the Bonferroni correction for multiple comparisons were used for overall comparisons between ventilation devices. Statistical analysis was done with a statistical software package (such as PASW Statistic 18, available from SPSS of Chicago, Ill., USA). A $p<0.05$ was considered statistically significant. Regarding the values of $V_T$, only differences that were both statistically significant ($p<0.05$) and clinically important ($>10\%$) were reported.

Figures 4A, 4B, 4C, 4D, 4E, 4F:
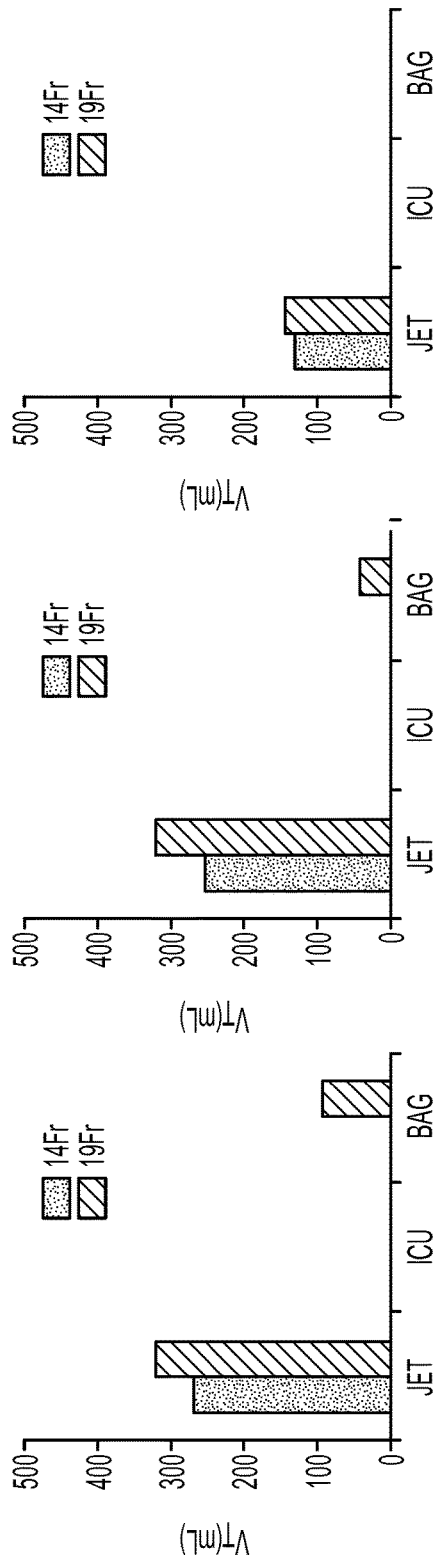
FIGS. 4A-4F are charts of test results using the test setup of FIG. 3.

The mean $V_T$s generated by Jet, ICU vent, and Bag in both conventional catheters and cuffed ACs 100 are presented in FIGS. 4A-4F. Using the conventional catheter, FIGS. 4A-4C show that Jet ventilation provided a mean $V_T$ of 262 ml (range: 40 ml to 631 ml) with 19 Fr and 220 ml (24 ml to 634 ml) with 14 Fr across all lung mechanics settings. Both Bag and ICU ventilators did not generate effective $V_T$ with conventional catheters, as shown in FIGS. 4A-4C.

With a cuffed AC 100 such as that described above, the ICU vent and Bag were able to generate $V_T$s of 373 ml (range: 224 ml to 487 ml) with 19 Fr and 232 ml (130 ml to 370 ml) with 14 Fr, as shown in FIGS. 4A-4C. Jet could not effectively be used with the cuffed AC 100 because the inflatable cuff 124 did not deflate during exhalation, leading to very high auto PEEP levels. (This phenomenon occurs with the Jet system because the driving pressure of the Jet does not commonly return to zero unless the catheter or other tube used with the Jet opens to ambient pressure, which does not generally occur. In contrast, when an ICU vent is used, the driving pressure commonly returns to zero at the end of the inspiratory phase unless PEEP is set up.) With the cuffed ACs 100, $V_T$s were greater with the larger AC than with the smaller AC ($p<0.01$).

With the conventional catheters, $V_T$ with Jet under normal and obstructive lung mechanics did not differ significantly, but the restrictive lung model yielded smaller $V_T$ than those of normal and obstructive models in all scenarios and with both conventional catheter sizes ($p<0.01$). With cuffed ACs 100, $V_T$s did not differ significantly across lung mechanics settings in both AC sizes (FIGS. 4 D-F).

Figure 5A:
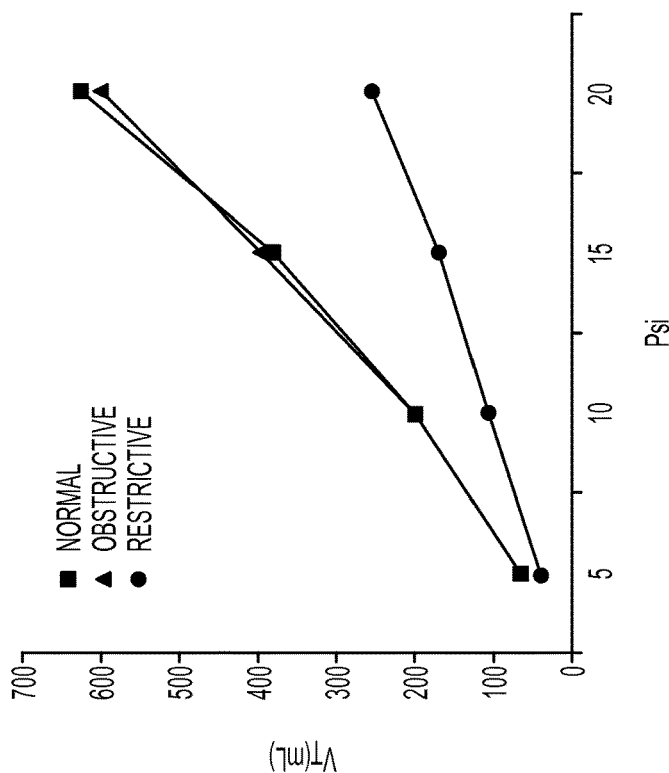
FIGS. 5A-5B are charts of test results using the test setup of FIG. 3.
Figure 5B:
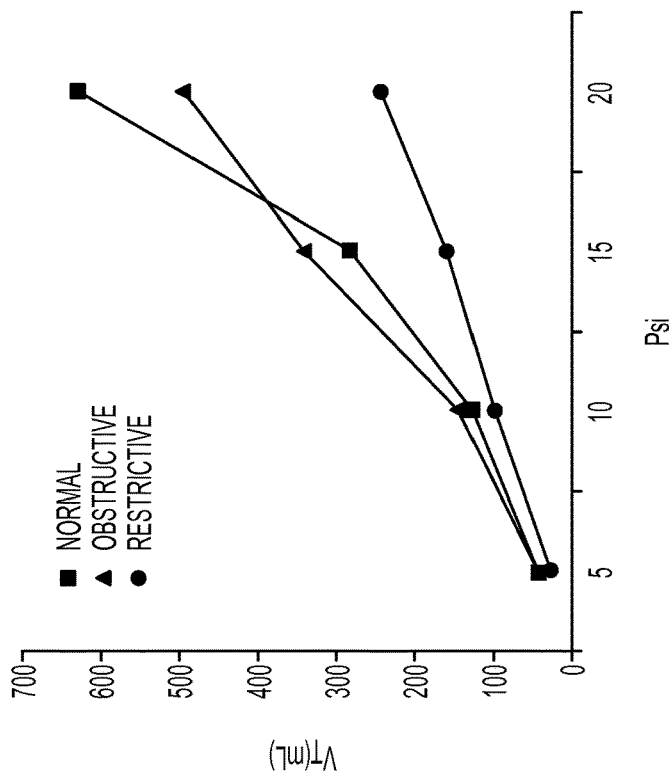

FIGS. 5A-5B show $V_T$s achieved with different driving pressures using Jet and conventional catheters. With both the 14 Fr (FIG. 5A) and 19 Fr (FIG. 5B) conventional catheters, driving pressures of greater than 10 psi were needed to generate effective $V_T$ in all lung mechanics settings.

In conventional catheters, longer inspiratory times did not generate significantly greater $V_T$ with Jet. For all I:E ratios studied, the ICU vent and Bag failed to generate effective $V_T$ in both 14 Fr and 19 Fr conventional catheters, as shown in FIGS. 6A-6B. In cuffed ACs 100, longer inspiratory times generated greater $V_T$ with ICU vent and Bag ($p<0.01$), as shown in FIGS. 6C-6D.

Figure 7B:
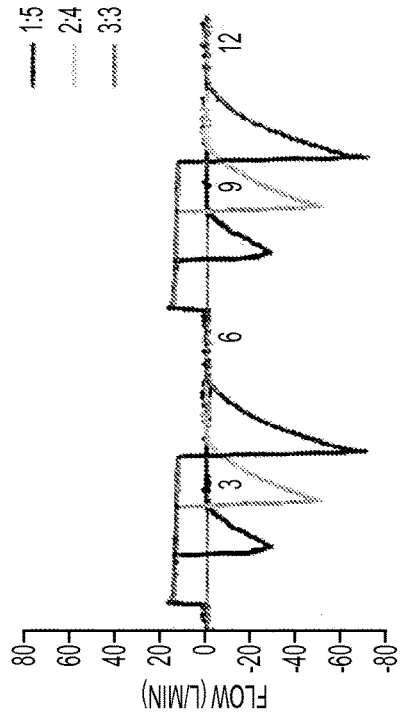
FIGS. 7A-7D are charts of test results using the test setup of FIG. 3.
Figure 7D:
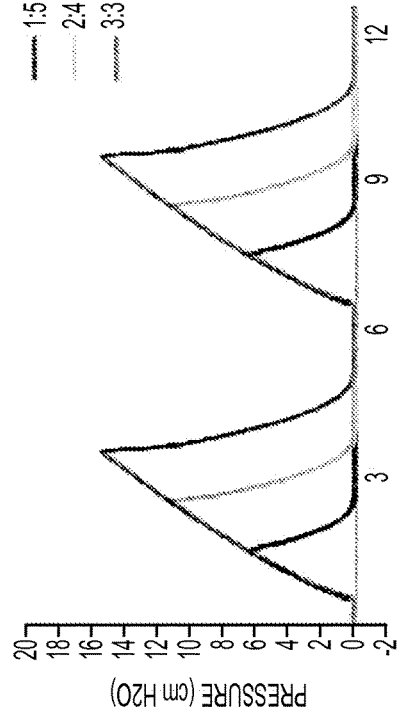
Figure 7A:
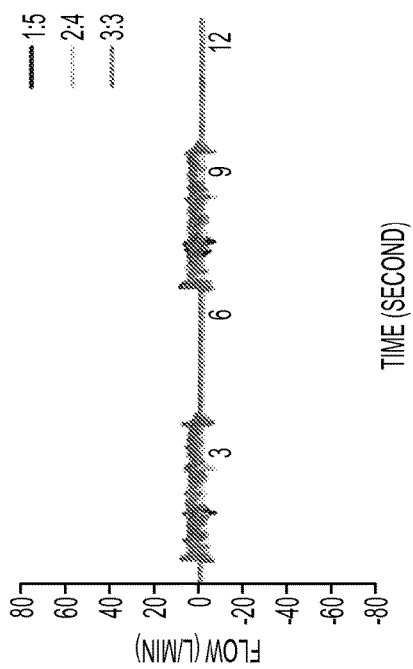
Figure 7C:
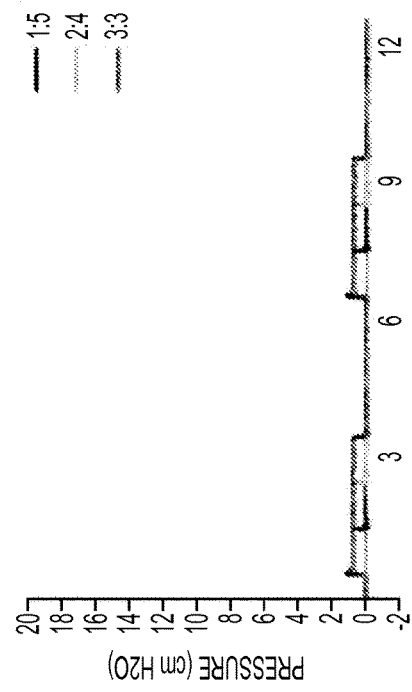

Representative waveforms of airway flow and pressure with ICU70 are shown in FIGS. 7A-7D. (FIGS. 7A and 7C depict the use of a conventional catheter, and FIGS. 7B and 7D were generated using a cuffed AED 100.) As inspiratory time increased, peak inspiratory flow and airway pressure increased using cuffed ACs 100. However with conventional catheters, peak inspiratory flow and airway pressure did not differ with increased inspiratory times and failed to achieve greater than 1 cmH$_2$O of airway pressure.

Some conclusions of this study are: (i) Jet generates effective ventilation using conventional catheters, but requires driving pressures greater than 10 psi; (ii) ICU vent and Bag were unable to generate effective ventilation using conventional catheters; and (iii) ICU vent and Bag were able to generate effective ventilation using inflatable-cuffed ACs 100. These results indicate that cuffed ACs 100 may enable practitioners to use ordinary ICU vent and/or Bag ventilators and achieve effective $V_T$s at much lower driving pressures than with the Jet.

With conventional catheters, only Jet was able to generate effective ventilation, but required high driving pressure of at least 10 psi. Because the ICU vent and Bag provided much lower driving pressures than the Jet, these two devices could not generate effective $V_T$ with conventional catheters. The open airway simulated by the experimental setup requires a high driving pressure to maintain airway pressure and ventilation. A previous study has compared the efficacy of anesthesia machines' flush valves as a source for jet ventilation with a conventional catheter. The machine with the lowest driving pressure at 7 psi (492 cmH$_2$O) was unable to generate any $V_T$ and thus was considered an unacceptable power source for jet ventilation. Machines with greater driving pressures 18 and 50 psi were able to generate greater $V_T$ and provide at least partial ventilatory support in most clinical scenarios.

In contrast, this study shows, for example, that an effective $V_T$ can be achieved with driving pressures as low as 25 cmH$_2$O by using a cuffed AC 100. The ability of the inflatable cuff 124 to assist with achieving effective $V_T$ can be shown with reference to FIG. 7A-7D. With the conventional catheter, the pressure gradient between the trachea 144 and the open oropharynx prevents ventilation with low driving pressures. The tracheal inner wall 142 and conventional catheter create simultaneous co-axial flow during inspiration. As a result, turbulent flow and low airway pressure were established without ventilation (FIGS. 7A and 7C).

By inflating the inflatable cuff 124, the open system of the experimental setup transforms into a closed system through use of the cuffed AC 100. The ability of the inflatable cuff 100 to prevent air from leaking out of the open tracheal model helps allows for airway pressure and flow to increase with inspiratory time, generating greater $V_T$, as shown in FIGS. 7B and 7D. The ability to ventilate patients using lower pressure settings may reduce the risk of barotraumas. In addition, cuffed ACs 100 may be used with commonly available ventilators (ICU vent and Bag).

The $V_T$ generated with Jet and conventional catheters significantly differed with lung mechanics settings, while the ICU vent and Bag used with cuffed ACs 100 generated similar $V_T$ with all lung mechanics. Although driving pressures with conventional catheters may need to be adjusted depending on the compliance of the lungs, cuffed ACs 100 could be used in a variety of patients without altering pressure settings.

The ability of the cuffed AC 100 to generate $V_T$ depends, at least in part, on inspiration time. This is because the high resistance generated by the small inner diameter of the tube lumen 108 prevents airway pressure from quickly being established in the lung model. In this adult model, an inspiratory time of 2 to 3 seconds generated effective $V_T$.

In conclusion, cuffed ACs 100 seem to be able to generate effective ventilation with ICU vent and Bag ventilators at much lower driving pressures than a Jet ventilator. Jet ventilation with a non-cuffed conventional catheter seems to be able to provide ample $V_T$, but requires driving pressure of at least 10 psi.

The inflation/deflation cycle of the inflatable cuff 124 of the AC 100 may be helpful in providing a transient and reversible pressure on the mucosa of the trachea 144. In this manner, the mucosa of the trachea 144 may have improved blood supply during expiration as compared to a traditional long-term-inflated cuff. In addition, constant insufficiency of blood perfusion within the trachea 144 structures and mechanical/friction damage to the trachea may be avoided through use of the present invention.

While aspects of the present invention have been particularly shown and described with reference to the preferred embodiment above, it will be understood by those of ordinary skill in the art that various additional embodiments may be contemplated without departing from the spirit and scope of the present invention. For example, the AC 100, or components thereof, may have any suitable shape, cross-sectional or otherwise. The AC 100, or components thereof, may self-expand through the use of memory alloy materials, magnetic attraction/repulsion, or any other desired mechanism. The specific methods described above for using the AC 100 are merely illustrative; one of ordinary skill in the art could readily determine any number of tools, sequences of steps, or other means/options for placing the above-described apparatus, or components thereof, into positions substantively similar to those shown and described herein. One of ordinary skill in the art can readily provide a tube lumen 108, plug lumen 134, side holes 122, inflatable cuff 124, and/or any other component of the AC 100 having a desired size, shape, material, and/or any other property to adjust the aforementioned fluid flow characteristics in a desired manner for a particular application of the present invention. The AC 100, or any components thereof, may be advanced into a bronchus as appropriate to provide desired one-lung ventilation. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. Unless otherwise specifically stated, contact could be either direct or indirect, though even directly-contacting structures may be shown spaced apart in the Figures for clarity of depiction. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An airway catheter ("AC"), comprising:
   an elongate, flexible catheter tube having a proximal tube end face and a longitudinally spaced distal tube end face in mutual fluid communication with a tube lumen extending longitudinally through the tube and defined laterally by a tube wall extending between the proximal and distal tube end faces, the tube wall having an inner tube wall surface and a laterally spaced outer tube wall surface, the distal tube end face and a minority portion of the tube wall directly longitudinally adjacent to the distal tube end face collectively forming a distal tube end region;
   a plurality of side holes extending laterally through the tube wall between the inner and outer tube wall surfaces, all of the side holes being located in the distal tube end region;
   an inflatable cuff secured to the outer tube wall surface at two longitudinally spaced circumferences of the outer tube wall surface in the distal tube end region such that an inner volume of the cuff is in fluid communication with the tube lumen via all of the plurality of side holes, the inflatable cuff being configured for selective adjustment between inflated and deflated conditions; and a reduced-diameter resistor plug having a proximal plug end face and a laterally spaced distal plug end face in mutual fluid communication with a plug lumen extending longitudinally through the resistor plug and defined laterally by a plug wall extending between the proximal and distal plug end faces, the plug lumen having a substantially smaller inner diameter than an inner diameter of the tube lumen in the distal tube end region, the plug wall having an inner plug wall surface and a laterally spaced outer plug wall surface, the resistor plug being maintained within at least a portion of the tube lumen in the distal tube end region with an outer plug wall surface being at least partially in compressive contact with the inner tube wall surface;

wherein the resistor plug is maintained within at least a portion of the tube lumen in the distal tube end region with an outer plug wall surface being at least partially in compressive contact with the inner tube wall surface and with the distal plug end face being located distally from the distal tube end face.

2. The AC of claim 1, wherein the tube lumen is substantially of constant diameter and cross-section along an entire longitudinal length thereof.

3. The AC of claim 1, wherein the plug lumen is substantially of constant diameter and cross-section along an entire longitudinal length thereof.

4. The AC of claim 1, wherein the proximal tube end face is configured for operative connection to a ventilation fluid source to place the tube lumen in fluid communication with the ventilation fluid source.

5. The AC of claim 4, wherein, when the tube lumen is in fluid communication with the ventilation fluid source, ventilation fluid from the ventilation fluid source flows in a first, distally oriented direction through the tube lumen, the diameter of the plug lumen causes a first elevated ventilation fluid pressure in a portion of the tube lumen longitudinally coincident with at least a portion of the distal tube end region by resisting passage of the ventilation fluid through the plug lumen, and the first elevated ventilation fluid pressure caused thereby forces at least a portion of the ventilation fluid through at least one side hole and into the inflatable cuff to urge the inflatable cuff toward the inflated condition.

6. The AC of claim 5, wherein the inflatable cuff is configured to accept a predetermined volume of ventilation fluid from the plurality of side holes and, when the inflatable cuff has achieved the inflated condition through presence of the ventilation fluid within the inflatable cuff, to resist flow through the side holes of ventilation fluid in excess of the predetermined volume of ventilation fluid, and wherein the flow resistance of the inflatable cuff causes a second elevated ventilation fluid pressure, higher than the first elevated ventilation fluid pressure, in a portion of the tube lumen longitudinally coincident with at least a portion of the distal tube end region, the second elevated ventilation fluid pressure urging ventilation fluid distally through the plug lumen and out of the AC from the distal tube and plug end faces.

7. The AC of claim 6, wherein the ventilation fluid urged distally through the plug lumen and out of the AC from the distal tube and plug end faces is operative to raise an ambient fluid pressure in an ambient space distally located with respect to the AC.

8. The AC of claim 7, wherein when the tube lumen is in fluid communication with the ventilation fluid source, the fluid pressure within the tube lumen is selectively adjusted to have a lower pressure than the ambient fluid pressure in the ambient space distally located with respect to the AC, and the lower pressure within the tube lumen causes ventilation fluid to be drawn through the side holes from the inflatable cuff, thus urging the inflatable cuff toward the deflated condition.

9. The AC of claim 8, wherein at least partial deflation of the inflatable cuff and the ambient fluid pressure cooperatively urge ventilation fluid from the ambient space to flow in a second, proximally oriented direction past the outer tube wall.

10. The AC of claim 8, wherein at least the ambient fluid pressure urges ventilation fluid from the ambient space to flow in a second, proximally oriented direction through the tube lumen.

* * * * *